United States Patent
Greenspoon

(10) Patent No.: US 10,456,357 B2
(45) Date of Patent: Oct. 29, 2019

(54) ORALLY ADMINISTRABLE FORMULATION

(71) Applicant: Allen Greenspoon, Hamilton (CA)

(72) Inventor: Allen Greenspoon, Hamilton (CA)

(*) Notice: Subject to any disclaimer, the term of this patent is extended or adjusted under 35 U.S.C. 154(b) by 0 days.

(21) Appl. No.: 15/806,928

(22) Filed: Nov. 8, 2017

(65) Prior Publication Data

US 2018/0064645 A1 Mar. 8, 2018

Related U.S. Application Data

(62) Division of application No. 15/222,019, filed on Jul. 28, 2016, now Pat. No. 9,833,408.

(51) Int. Cl.
*A61K 9/68* (2006.01)
*A61K 31/05* (2006.01)
*A61K 31/352* (2006.01)
*A61K 31/4468* (2006.01)
*A61K 31/485* (2006.01)
*A61K 36/185* (2006.01)

(52) U.S. Cl.
CPC ............ *A61K 9/0058* (2013.01); *A61K 31/05* (2013.01); *A61K 31/352* (2013.01); *A61K 31/4468* (2013.01); *A61K 31/485* (2013.01); *A61K 36/185* (2013.01)

(58) Field of Classification Search
CPC .................................................. A61K 31/352
USPC .................................. 424/465, 456; 514/454
See application file for complete search history.

(56) References Cited

U.S. PATENT DOCUMENTS

| | | | |
|---|---|---|---|
| 4,816,265 A | 3/1989 | Cherukuri et al. | |
| 6,132,762 A * | 10/2000 | Cristobal | A61K 9/0014 |
| | | | 424/401 |
| 6,503,532 B1 | 1/2003 | Murty et al. | |
| 6,946,150 B2 | 9/2005 | Whittle | |
| 8,481,091 B2 | 7/2013 | Ross | |
| 9,095,555 B2 * | 8/2015 | Winnicki | A61K 9/127 |
| 2004/0162336 A1 * | 8/2004 | McPhillips | A61K 9/0078 |
| | | | 514/454 |
| 2009/0181080 A1 * | 7/2009 | Kottayil | A61K 9/0014 |
| | | | 424/456 |

FOREIGN PATENT DOCUMENTS

| | | | | |
|---|---|---|---|---|
| CA | 2659775 | | 2/2007 | |
| CA | 2719830 | | 10/2009 | |
| CA | 2904968 | | 10/2014 | |
| CA | 2937471 | | 9/2016 | |
| GB | 2391865 | * | 2/2004 | ........... C07D 311/78 |
| WO | 2009/120080 | | 3/2009 | |

OTHER PUBLICATIONS

PCT International Search Report—PCT/CA2017/050904.

* cited by examiner

*Primary Examiner* — Walter E Webb
(74) *Attorney, Agent, or Firm* — Gowling WLG (Canada) LLP

(57) ABSTRACT

An orally administrable chewing gum formulation is provided comprising a pharmaceutically acceptable gum base and particles of a pharmaceutical agent ranging in size from about 50 to about 2000 μm, wherein the formulation comprises about 0.5-30% by wt of the pharmaceutical agent particles. A liquid formulation comprising particles of a pharmaceutical agent is also provided.

10 Claims, No Drawings

ORALLY ADMINISTRABLE FORMULATION

FIELD OF THE INVENTION

The present invention, generally relates to orally administrable formulations, such as a chewing gum and aqueous-based formulations.

There has been considerable effort in formulating a chewing gum that can deliver pharmaceutical agents at a level achieved by other administrable routes. For example, cannibinoids and derivatives thereof, may be consumed by smoking marijuana. However, as is known, smoking results in serious deleterious effects, including various lung diseases, and is a major cause of environmental pollution. Also, smoking is not an appropriate means for cannabinoid administration to certain populations, e.g. children and elderly persons.

Accordingly, it would be desirable to develop alternative means to deliver pharmaceutical agents such as cannabinoid derivatives for treatment of pain and other ailments.

SUMMARY OF THE INVENTION

A novel orally administrable gum formulation comprising one or more pharmaceutical agents has now been developed which provides rapid release of the pharmaceutical agents for absorption into the circulatory system of a mammal.

Thus, in one aspect of the invention, an orally administrable chewing gum formulation is provided comprising a pharmaceutically acceptable gum base and particles of a pharmaceutical agent ranging in size from about 50 to about 2000 μm, wherein the formulation comprises about 0.5-30% by wt of the pharmaceutical agent particles.

In another aspect, a chewing gum formulation comprising first and second chewing gum modules is provided. The first chewing gum module comprises a first chewing gum composition comprising at least a first pharmaceutical agent combined with a gum base, and the second chewing gum module comprises a second chewing gum composition comprising a second pharmaceutical agent or other agent combined with a gum base, wherein the first chewing gum composition is different in composition to the second chewing gum composition.

In a further aspect, an aqueous-based formulation is provided comprising water, alcohol and/or propylene glycol in an amount in the range of about 60-99% by wt and pharmaceutical agent-containing particles in an amount in the range of about 1-40% by wt.

These and other aspects of the invention will become apparent in view of the following detailed description.

DETAILED DESCRIPTION OF THE INVENTION

In one aspect, an orally administrable chewing gum formulation is provided comprising a pharmaceutically acceptable gum base and particles of a pharmaceutical agent ranging in size from about 50 to about 2000 μm, wherein the formulation comprises about 0.5-30% by wt of the pharmaceutical agent particles.

The composition is not particularly restricted with respect to the pharmaceutical agent. Examples of pharmaceutical agents that may be incorporated in the present formulation include, but are not limited to:

antimicrobial agents, such as triclosan, cetyl pyridium chloride, domiphen bromide, quaternary ammonium salts, zinc compounds, sanguinarine, fluorides, alexidine, chlorhexidine, octonidine, EDTA, and the like;

non-steroidal anti-inflammatory drugs, such as aspirin, acetaminophen, ibuprofen, ketoprofen, diflunisal, fenoprofen calcium, naproxen, tolmetin sodium, indomethacin, and the like;

anti-tussives, such as benzonatate, caramiphen edisylate, menthol, dextromethorphan hydrobromide, chlophedianol hydrochloride, and the like;

decongestants, such as pseudoephedrine hydrochloride, phenylepherine, phenylpropanolamine, pseudoephedrine sulfate, and the like;

anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, cetirizine, levo cetirizine and the like;

expectorants, such as guaifenesin, ipecac, potassium iodide, terpin;

anti-diarrheals, such a loperamide, and the like;

H2-antagonists, such as famotidine, ranitidine, and the like;

proton pump inhibitors, such as omeprazole and lansoprazole;

nonselective CNS depressants, such as aliphatic alcohols, barbiturates and the like;

nonselective CNS stimulants such as caffeine, nicotine, nicotine polacrilex, nicotine in combination with alkaline agents, strychnine, picrotoxin, pentylenetetrazol and the like;

drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;

antiparkinsonism drugs such as levodopa, amantadine and the like;

analgesic-antipyretics such as salycilates, phenylbutazone, indomethacin, phenacetin and the like;

psychopharmacological drugs such as chlorpromazine, methotrimeprazine, haloperidol, clozapine, reserpine, imipramine, tranylcypromine, phenelzine, MC-4 receptor antagonist, lithium and the like;

hypnotics, sedatives, antiepileptics, awakening agents;

vitamins and minerals;

amino acids and peptides;

sildenafil citrate;

antidiabetic drugs, e.g. metformin, metformin HCL, glyburide and insulin secretart agent, insulin stimulators, fat metabolizers, carbohydrates metabolizers, insulin, cholesterol lowering agents like statins, exenatide, GLP-1, etc.

opioid analgesics such as alfentanil, allylprodine, alphaprodine, anileridine, benzylmorphine, bezitramide, buprenorphine, butorphanol, clonitazene, codeine, cocaine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiannbutene, ethylmorphine, etonitazine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, diamorphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, mixed mu-agonists/antagonists, mu-antagonist combinations, mixtures of any of the foregoing, and the like. The opioid analgesic may be in the form of the free base, or in the form of a pharmaceutically acceptable salt, or in the form of a pharmaceutically acceptable complex; and pharmaceutical agents derived from plant material, such as cannibinoids and derivatives thereof, terpenes, Paclitaxel™, plant-derived vitamins, plant-derived proteins (soya, lantils), and the like.

The term "cannabinoid" and "cannabinoid derivative" is used herein to refer to a class of diverse chemical compounds that act on cannabinoid receptors, e.g. cannabinoid receptor type 1 (CB1) and cannabinoid receptor type 2 (CB2), in cells that repress neurotransmitter release in the brain. Cannibinoids include the endocannabinoids (produced naturally in the body by humans and animals, such as arachidonoyl-ethanolamide (anandamide), 2-arachidonoyl glycerol (2-AG) and arachidonyl glyceryl ether (noladin ether)); the phytocannabinoids (found in cannabis and some other plants such as tetrahydrocannabinol (THC), cannabidiol (CBD) and cannabinol (CBN); synthetic cannabinoids (manufactured artificially), and functionally equivalent derivatives and analogues of any of these. Examples of cannabinoids include, but are not limited to, cannabidiol (CBD), cannabidiol acid (CBDA), cannabinol (ON), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), naphthoylindoles such as JWH-018, JWH-073, JWH-398, JWH-200, MN-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenoles such as CP 47,497-C8 and CP 47,497; HU-210 and 3-dimethylnepty 11 carboxylic acid homologine 8. Cannibinoids also include tetrahydrocannabinoids and analogs thereof, namely, delta-9 tetrahydrocannabinol (THC or dronabinol) and functionally equivalent compounds, including analogs and derivatives thereof such as delta-8 tetra hydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018, JWH-073, CP-55940, dimethylheptylpyran, HU-210, HU-331, 5R144528, WIN 55,212-2, JWH-133, levonantradol, and AM-2201. Mixtures of any of the above cannabinoids is also encompassed. The term "functionally equivalent" as it relates to analogs and derivatives of a cannabinoid refers to compounds which bind a cannabinoid receptor, and/or which exhibit the same or similar therapeutic effect, e.g. at least about 50% of the activity of the cannabinoid from which it is derived.

For purposes of the present invention, the term "cannabinoid" includes naturally occurring and non-natural derivatives of cannabinoids which can be obtained by derivation of natural cannabinoids. In other words, the cannabinoid used in the formulations of the invention may be natural, semisynthetic, or synthetic. The cannabinoid may be included in its free form, or in another pharmaceutically acceptable form such as a salt; an acid addition salt of an ester; an amide; enol forms; different isomeric forms such as an enantiomer, diastereoisomer or tautomer; racemic mixtures; a prodrug (such as THC-hemisuccinate); or a complex, either in pure form or in admixture. Derivatives of a cannabinoid also include derivatives in which there is substitution of one atom, molecule or group by another, such as 11-hydroxy-delta-8-tetrahydrocannabinol and 11-hydroxy-delta-9-tetrahydrocannabinol.

Cannabinoids have a wide range of medical uses, and different subgroups or single cannabinoids have beneficial effects on certain conditions, while other subgroups or individual cannabinoids have beneficial effects on other conditions. For example, THC is the main psychoactive cannabinoid produced by Cannabis and is well-characterized for its biological activity and potential therapeutic application in a broad spectrum of diseases. CBD, another major cannabinoid constituent of Cannabis, acts as an inverse agonist of the CB1 and CB2 cannabinoid receptors and does not produce psychoactive effects in humans. Thus, CBD is reported to exert analgesic, antioxidant, anti-inflammatory, and immunomodulatory effects. Accordingly, formulations comprising mixtures of cannabinoids, such as THC and CBD mixtures, may be useful to treat complex conditions.

Cannabinoids may be extracted from the cannabis plant using methods well-established in the art. Many of the cannibinoids may also be prepared using standard chemical synthetic methods. Some of these compounds are also commercially available.

Terpenes, including terpenoids, another class of compounds that are produced by cannabis plants, also have medicinal properties, and are useful for inclusion in the present formulation. Examples of such terpenes include, but are not limited to, humulene, pinene, linalool, myrcene, limonene and caryophyllene. Some medical benefits attributable to terpenes isolated from cannabis include treatment of sleep disorders, psychosis, anxiety, epilepsy and seizures, pain, microbial infections (fungal, bacterial, etc.), cancer, inflammation, spasms, gastric reflux, depression, and asthma. Terpenes may lower the resistance across the blood-brain barrier, act on cannabinoid receptors and other neuronal receptors, stimulate the immune system, and/or suppress appetite.

The amount of pharmaceutical agent in the formulation will vary with the particular selected pharmaceutical agent, the form in which the pharmaceutical is incorporated within the formulation, the condition to be treated and the effective dosage. In some embodiments, the formulation will comprise an amount of the pharmaceutical in the range of about 1 mg to 1000 mg, preferably 1-500 mg, such as 1-250 mg.

Prior to incorporation of the pharmaceutical agent in the formulation, the pharmaceutical agent may be prepared into fine particles ranging in size from about 50 to about 2000 µm. This may involve crushing the pharmaceutical to form the desired particles. For pharmaceutical agents obtained from plant material, such as cannabinoids, terpenes and derivatives thereof present in the Cannabis plant, the plant material (e.g. leaves) may be prepared into fine particles, for example, in which at least 50% by weight, preferably at least 75% by weight of the particles have a size in the range of about 50 and 2000 µm, preferably between 100 and 1200 µm, such as between 300 and 750 µm. The pharmaceutical agent-containing particles may be included in the formulation in an amount of about 0.5 and 30% by weight of the chewing gum formulation, for example, an amount of about 2-25% by weight, such as 3-22%, 4-20% or 5-15% by weight of the chewing gum formulation. The weight of pharmaceutical agent-containing particles in the chewing gum formulation, thus, is at least about 10 mg, such as at least about 20 mg, 30 mg or 40 mg.

If the pharmaceutical agent is derived from plant material, preferably the plant material is first washed and/or treated, for example by exposure to a heat steaming process, to reduce the viable bacterial and fungal count therein to a level below 10,000 CFU/g (colony-forming units per gram), such as below 1,000 or below 100 CFU/g.

The combination of pharmaceutical-containing particles, e.g. as prepared from plant material, with the gum base additionally provides the benefit that fibrous material within the particles is retained in the gum base, and is excluded from absorption into the human body (assuming the gum is not swallowed), while the beneficial medicinal agents are released from the gum on chewing, for rapid absorption into the body.

It has been determined that the water content of the plant material affects the properties of the chewing gum formulation, and release rate of active pharmaceutical agents within the plant material. For example, plant material with a greater water content may enhance ease of handling the plant material and the particles prepared therefrom, as well as to provide a formulation that possesses a more desirable taste and texture, including softness. In addition, the release rate of pharmaceutical agents from particles derived from plant material (such as *Cannabis* leaves) may be improved and/or customized by selection of plant material having a certain water content. Generally, the water content of plant material for use to prepare pharmaceutical agent-containing particles is at least about 10%, and preferably in the range of about 10-50%.

The formulation additionally comprises a gum base. The components of the gum base may vary substantially depending on the desired masticatory and other sensory characteristics of the final product. However, typically, the gum base comprises: 5 to 80% by weight elastomer, 5 to 80% by weight elastomeric plasticizers, 0 to 40% by weight of wax, 5 to 35% by weight softener, 0 to 50% by weight filler, and 0 to 5% by weight of additional adjuvants such as antioxidants, colourants, sweetener, flavourant, preservative, etc.

The gum base may comprise about 5 to about 95 percent, by weight, of the formulation, and more commonly, the gum base comprises 10 to about 60 percent, by weight, of the formulation. It has been found that the amount of gum base in the chewing gum influences the retention of pharmaceutical-containing particles or the retention of particle fibers. The higher the gum base content, the better the retention of particles and fibers in the gum base after chewing.

Elastomers provide the rubbery, cohesive nature of the gum. Elastomers suitable for use in the gum base and gum of the present invention may be naturally-occurring or synthetic elastomers. Elastomers may be any water-insoluble polymer known in the art. Examples of suitable elastomers include, but are not limited to, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene (butyl rubber), isobutylene-isoprene copolymers, polyethylene, polyvinyl acetate and the like, and mixtures thereof.

Elastomeric plasticizers vary the firmness of the gum base. Examples of elastomer plasticizers for inclusion in the gum base include, but are not limited to, n-butyl stearate; oleic acid; mono-, di-, or tri-glyceryl esters of the saturated or unsaturated fatty acids of oleic acid, caprylic acid, butyric acid, capric acid, caproic acid and lauric acid; mineral oil, liquid petroleum hydrocarbons, squalane, squalene, castor oil and other ricinoleate derivatives; diethylene or propylene glycols and derivatives; tributyl acetyl citrate, tributyl citrate, lecithin, coconut oil, glyceryl tributyrate, Zn laurate, Ca stearate, propylene glycol monostearate, propylene glycol monolaurate, fatty acids, butyl sebacate, butyl benzyl sebacate, diacetyl tartaric acid esters of mono- and diglycerides of edible fat oils or edible fat forming acids; acetylated monoglyceride; petrolatum, stearyl monoglyceride citrate, limonene, polylimonene, natural waxes, butyl lactate, and butyl oleate.

Natural or synthetic resins may be included in the gum base in an amount ranging from 35-45% by wt. Examples include natural rosin esters (often referred to as ester gums), such as glycerol esters of partially hydrogenated rosins, glycerol esters of polymerised rosins, glycerol esters of partially dimerized rosins, glycerol esters of tally oil rosins, penta erythritol esters of partially hydrogenated rosins, methyl esters of rosins, partially hydrogenated methyl esters of rosins, and penta erythritol esters of rosins; and synthetic resins such as terpene resins derived from alpha-pinene, beta-pinene, and/or d-limonene, and natural terpene resin.

The gum base also includes a softener. Examples of suitable softeners include, but are not limited to, glycerin (glycerol) and most vegetable oils, which help to retain the proper amount of moisture in the gum base. In addition, ingredients such as mannitol and sorbitol may also assist with softening of the gum base.

The gum base may, if desired, include one or more fillers/texturisers including as examples, magnesium and calcium carbonate, sodium sulphate, ground limestone, silicate compounds such as magnesium and aluminum silicate, kaolin and clay, aluminum oxide, aluminum phosphate silicium oxide, talc, titanium oxide, mono-, di- and tri-calcium phosphates, cellulose polymers, such as wood fibers, mineral oil such as paraffin oil, plant saponins from Quillaia, soybean or polygala senega, and combinations thereof. The filler may preferably be hydrophobic.

The gum base may additionally include a wax. Suitable waxes include microcrystalline waxes which contain isoparaffinic (branched) hydrocarbons and naphthenic hydrocarbons such as Microwax™ 1750, Microwax™ 820, Paramelt® HMP (a blend of refined mineral hydrocarbon waxes having a high melting point and a low oil content), Paramelt® LMP (a low melting point, low oil content microwax), and Microwax™ ZG.

Once the gum base is prepared by mixing the selected components, it may be combined with one or more optional ingredients as follows, and the selected pharmaceutical agent.

The formulation may optionally include one or more buffers which facilitate release of pharmaceutical agent from the particles and enhances bioavailability of the pharmaceutical agent, e.g. cannabinoids, terpenes and/or derivatives thereof, in the oral cavity. Examples of suitable buffers include a carbonate, such as monocarbonate, bicarbonate or sesquicarbonate; glycerinate; phosphate; glycerophosphate; acetate; glyconate or citrate of an alkali metal, such as potassium and sodium, e.g. trisodium and tripotassium citrate; ammonium, tris buffer, amino acids, and mixtures thereof. The buffer may be microencapsulated or otherwise coated as granules with polymers and/or lipids being less soluble in saliva than the buffer. Such microencapsulation controls the dissolution rate of the buffer to permit it to effectively facilitate pharmaceutical agent release. Buffer is generally included in an amount of about 5% by wt or less of the formulation.

The formulation may comprise one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, menthol, peppermint, wintergreen, spearmint, eucalyptus, mint, or any combination thereof. The formulation may also optionally comprise bright leaf, burley-leaf, oriental-leaf tobacco, Dark air cured Burley, Flue cured Virginia, and dark fired Kentucky.

The formulation may comprise one or more of the following additional additives: a humectant, inorganic salts, antioxidants, protease inhibitors, emulsifiers, or colorants. Non-limiting examples of humectants include propylene glycol or glycerol. Examples of inorganic salts include sodium, potassium, calcium and zinc salts, especially sodium chloride, potassium chloride, calcium chloride, zinc chloride and sodium bicarbonate. Examples of antioxidants include tocopherol, deteroxime mesylate, methyl paraben, ethyl paraben, ascorbic acid and mixtures thereof. Examples of protease inhibitors include but are not limited to bacitracin and bacitracin derivatives such as bacitracin methylene disalicylates, soybean trypsin, and aprotinin. Examples of emulsifiers include lecithins (e.g. E322, E342), polyglycerol polyricinoleate (e.g. PGPR, E476), citric acid esters (e.g. E472c) and ammoniumphosphatide (e.g. E442) and sorbitan tristearate (e.g. STS, E492). Such additional additives may comprise combined between about 1 to 5 wt/wt % of the composition. Bacitracin and its derivatives preferably comprise between 1.5 and 2 wt/wt % of the total composition, while soyabean trypsin and aprotinin preferably comprise between about 1 and 2 wt/wt % of the total composition.

The formulation may include an anti-microbial agent. In one embodiment, the wafer comprises one or more essential oils that confer antimicrobial properties. Preferably, the amount of a selected essential oil for use in the formulation is sufficient to provide antimicrobial efficacy while not changing the physical characteristics of the wafer, e.g. an amount ranging from 0.01 to 15 wt % (but may exceed this range). Generally, an oil such as thymol, methyl salicylate and/or eucalyptol may be present in an amount of about 0.01 to about 4 wt % of the formulation, preferably about 0.50 to about 3.0 wt % of the formulation, and even more preferably from about 0.70 to about 2.0 wt % of the formulation. Menthol may be added in an amount ranging from about 0.01 to about 15 wt % of the formulation, preferably about 2.0 about 10 wt %, and even more preferably from about 3 to about 9 wt % of the formulation. The appropriate amount of a selected anti-microbial oil in the formulation can readily be determined by one of skill in the art.

Saliva stimulating agents may be added to the formulation according to the present invention. Examples of saliva stimulating agents include food acids such as citric, lactic, malic, succinic, ascorbic, adipic, fumaric and tartaric acids. Preferred food acids are citric, malic and ascorbic acids. The amount of saliva stimulating agents suitable for inclusion in the present formulation may range from about 0.01 to about 12 wt %, preferably about 1 wt % to about 10 wt %.

The formulation may also include one or more absorption enhancers, each in an amount of about 1-5% by wt of the formulation. Examples of enhancers include solubilization agents; charge modifying agents; pH control agents; degradative enzyme inhibitors; modulatory agents of epithelial junction physiology, such as nitric oxide (NO) stimulators, chitosan, or chitosan derivatives; vasodilator agents; selective transport-enhancing agents; stabilizing delivery vehicles, carriers, supports or complex-forming species with which exendin(s) is/are effectively combined, associated, contained, encapsulated or bound to stabilize the active agent for enhanced mucosal delivery; small hydrophilic penetration enhancers; emulsifiers, mucolytic or mucus clearing agents (e.g. mucoadhesive and mucosal delivery-enhancing agents); membrane penetration-enhancing agents such as e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer, (ix) sodium or a salicylic acid derivative, (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii)).

Examples of suitable mucoadhesives or mucosal delivery-enhancing agents as enhancers include Carbopol 934+HPC, Maize+Carbopol 907, HPC (hydroxypropyl cellulose), CMC or Na-CMC (carboxymethylcellulose), HPMC (hydroxypropylmethylcellulose), HEMA (hydroxyethyl metacrylate), Carbopol 907 crosslinked with sucrose, polyacrylic acids (PM), chitosans, lectins, polymethacrylate derivatives, hyaluronic acid, P(AA-co-PEG) monomethylether monomethacrylate, PAA-PVP (poly acrylic acid-poly vinyl pyrrilidone), PVP-PEG (polyethylene glycol), methylcellulose, pullulan, N-trimethyl chitosans, PDMAEMA (poly(dimethyl-aminoethyl methacrylate)), HEC (hydroxyethyl cellulose), Carbomer 940, Carbomer 971, polyethylene oxide, Dextrin, poly(methyl vinyl ether/maleic anhydride), Polycarbophil (acrylic acid crosslinked with divinyl glycol), PVP (poly vinyl pyrrilidone), agar, tragacanth, sodium alginate, karaya gum, MEC (methylethyl cellulose), HPC(hydroxy propyl cellulose), lectins, AB block copolymer of oligo (methyl methacrylate) and PAA, polymers with thiol groups, spheromers, thiomers, alginic acid sodium salt, Carbopol 974P (Carbomer), EC (ethylcellulose), dextran, guar gum, pectins, starch, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, and polyethers. In one embodiment, exendin is combined with one, two, three, four or more of the mucosal delivery-enhancing agents recited above.

The formulation may also include sweeteners, such as bulk sweeteners, sugar sweeteners, sugar substitute sweeteners, artificial sweeteners, high-intensity sweeteners, or any combination thereof. Suitable bulk sweeteners include both sugar and non-sugar sweetening components. Bulk sweeteners typically constitute from about 5 to about 95% by weight of the chewing gum, more typically about 20 to about 80% by weight such as 30 to 70% or 30 to 60% by weight of the gum. Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination. Sugar substitutes include, but are not limited to, sorbitol, mannitol, xylitol, hydrogenated starch hydrolysates, maltitol, isomalt, erythritol, lactitol and the like.

The present formulation may be prepared as follows. The gum base is prepared by combining the components of the gum base with stirring for a suitable period of time, e.g. about 30 minutes, generally with heat. The gum base is then blended with any optional additives, such as a selected buffer and any other desired additives at a temperature below 60° C., followed by blending with the pharmaceutical agent or pharmaceutical agent-containing particles.

In another embodiment, a gum product comprising two or more modules is provided. The first module comprises a gum base with at least one pharmaceutical agent or pharmaceutical agent-containing particles, and second or more modules each comprising a gum base with a second (or other) pharmaceutical agent or pharmaceutical agent-containing particles, or comprising one or more absorption enhancers such as a solubilization agent; charge modifying agent; pH control agents; degradative enzyme inhibitor; modulatory agent of epithelial junction physiology; vasodilator agents; selective transport-enhancing agents; stabilizing delivery vehicle; hydrophilic penetration enhancer; emulsifier; and mucolytic or mucus clearing agents. For example, a gum product comprising a first module comprising a gum base and one or more cannabinoids or derivatives such as THC and/or CBD, and a second module comprising gum base and a different cannabinoid or derivative, or an absorption enhancer such as a pH control agent.

It has surprisingly been found that substantial and effective amounts of pharmaceutical agent, such as cannabinoids or derivatives thereof, are released from a chewing gum formulation in accordance with the invention following chewing of the gum formulation for at least about 5-10 minutes, or longer. For example, at least about 40% of the pharmaceutical content in the chewing gum formulation is released from the chewing gum formulation within the first 10 minutes from initiation of a chewing process carried out on a chewing machine in accordance with European Pharmacopeia 4 th, ed. 2.9.25, with a phosphate buffer with a pH of 7.4. Moreover, it has been found that for pharmaceutical agents derived from plant material, at least 40% of the plant fibres in the pharmaceutical particles are retained in the chewing gum after the chewing gum has been chewed in accordance with European Pharmacopeia 4th, ed. 2.9.25 in a pH 7.4 phosphate buffer for 10 minutes.

In another aspect, an aqueous-based formulation is provided comprising water, alcohol and/or propylene glycol (which are stable at room or refrigerated temperatures) in a combined amount of about 60-99% by wt, and pharmaceutical agent-containing particles, such as Cannibis leaf particles containing cannabinoids, terpenes and/or derivatives, in an amount in the range of about 1-40% by wt. In one embodiment, the formulation comprises a pharmaceutical agent, and the following ingredients: (i) from about 0 to about 40% water, (ii) from about 15 to about 65% alcohol, preferably ethanol, and (iii) a co-solvent that is (a) propylene glycol from about 0% to about 50%, (b) polyethylene glycol from about 0 to about 50%, and/or (c) a combination of (a) and (b), the solution having a combined total of 100%, wherein the formulations are suitable for oral administration and have in vivo absorption variability of less than 50%.

The liquid formulation may include additional additives such as those identified above in the amounts specified. The liquid formulation possesses an improved in vivo absorption profile, with lower inter-subject variability, over existing cannabinoid formulations.

The liquid formulation may be administered orally, or may be formulated for administration by parental routes such as intravenous, intramuscular, intradermal, intraperitoneal, subcutaneous, spinal, intra-arterial, intrathecal, intracapsular, intraorbital, intracardiac, transtracheal, subcuticular, intraarticular, subcapsular, subarachnoid, intraspinal, epidural and intrasternal injection and infusion; and non-parenteral routes such as topical, epidermal or mucosal routes of administration, for example, intranasally, orally, vaginally, rectally, sublingually, transdermally or topically.

EXAMPLES

Example 1

Preparation of a Gum Base and Formulation with the Gum Base

The composition of a gum base is presented in Table 1. Amounts are given in wt % of the gum base composition.

TABLE 1

| Gum base composition | |
|---|---|
| | Wt % |
| Microcrystalline Wax | 78.08 |
| Butyl Rubber | 10.91 |
| Acetylated Monoglyceride | 9.09 |
| Talc | 1.92 |
| Total | 100% |

The composition of the chewing gum formulation including the gum base is presented in Table 2. Amounts are given in wt % of the chewing gum formulation.

TABLE 2

| Components of chewing gum formulation (by wt of the formulation) | |
|---|---|
| | Wt % |
| Gum Base | 28.00 |
| Sorbitol | 59.89 |
| Glycerin | 4.00 |
| Peppermint Flavor | 1.84 |
| Lecithin | 0.45 |
| Sweetener (Stevia or Xylitol) | 0.82 |
| Cannabinoids (THC + CBD 1:1) | 5.00 |
| Total | 100% |

The gum base was prepared as follows. The high-molecular weight elastomer (butyl rubber), plasticizer (acetylated monoglyceride) and wax were combined in a heated (about 120° C.) and running z-blade mixer and mixed for about twenty minutes to form the gum base.

To prepare the gum formulation, to a measured amount of gum base was added each of the ingredients (separately, in any order) followed by mixing. The pharmaceutical component (cannabinoid mix) was added last and mixed for about five-thirty minutes. The final product was emptied from the mixer into coated or lined pans, extruded or cast into any desirable shape.

Those skilled in the art will recognize that many variations of the above-described procedure may be followed.

The chewing gum formulation may optionally be coated by means of hard coating applied according to conventional coating methods. The pieces were visually evaluated and found to be visually acceptable.

Example 2

Preparation of an Opiate Reduction Formula (Opiate+THC+Cannabinoid)

A gum formulation comprising the gum base and other ingredients listed below was prepared as described in Example 1.

| Gum Base | Wt % |
| --- | --- |
| Microcrystalline Wax | 68.08 |
| Butyl Rubber | 7.91 |
| Acetylated Monoglyceride | 9.09 |
| Pectin | 5.00 |
| Pullulan | 3.00 |
| Talc | 1.92 |
| Total | 100% |

| Gum Formulation | Wt % |
| --- | --- |
| Gum Base from above | 18.00 |
| Sorbitol | 69.89 |
| Glycerin | 4.00 |
| Peppermint Flavor | 1.84 |
| Lecithin | 0.45 |
| Sweetener (Stevia or Xylitol) | 0.82 |
| Cannabinoids + Oxycontin + THC + CBD (0.5:0:0.7:1.) | 9.00 |
| Total | 100% |

Example 3

Preparation of an Opiate reduction formula (Opiate+THC+Cannabinoid)

A gum formulation comprising the gum base and other ingredients listed below was prepared as described in Example 1.

| Gum Base | Wt % |
| --- | --- |
| Microcrystalline Wax | 68.08 |
| Butyl Rubber | 7.91 |
| Acetylated Monoglyceride | 9.09 |
| Pectin | 5.00 |
| Gelatin | 5.00 |
| Pullulan | 3.00 |
| Talc | 1.92 |
| Total | 100% |

| Gum Formulation | WT % |
| --- | --- |
| Gum Base from above | 18.00 |
| Sorbitol | 69.89 |
| Glycerin | 4.00 |
| Peppermint Flavor | 1.84 |
| Lecithin | 0.45 |
| Sweetener (Stevia or Xylitol) | 0.82 |
| Cannabinoids + Fentanyl + THC + CBD )0.5:0:1.0:0.7.) | 9.00 |
| Total | 100% |

Example 4

Preparation of an Orally Dissolvable Chewing Gum (Swallowable) Formula

A gum formulation comprising the gum base and other ingredients listed below was prepared as described in Example 1.

| Gum Base | Wt % |
| --- | --- |
| Microcrystalline Wax | 68.08 |
| Butyl Rubber | 7.91 |
| Acetylated Monoglyceride | 9.09 |
| Pectin | 5.00 |
| Gelatin | 5.00 |
| Pullulan | 3.00 |
| Talc | 1.92 |
| Total | 100% |

| Gum Formulation | Wt % |
| --- | --- |
| Gum Base from above | 8.00 |
| Sorbitol | 77.89 |
| Glycerin | 5.00 |
| Peppermint Flavor | 2.84 |
| Lecithin | 0.45 |
| Sweetener (Stevia or Xylitol) | 0.82 |
| Cannabinoids + Oxycontin + THC + CBD )0.5:0:0.7:1.) | 9.00 |
| Total | 100% |

Example 5

Preparation of an Oral Solution, Drops or Spray

An excipient solution was prepared by dissolving butylated hydroxyl anisole (BHA), sucralose, methyl paraben and propyl paraben in dehydrated ethyl alcohol in an air tight tank/container sparged with nitrogen for about fifteen (15) to thirty (30) minutes. PEG 400, propylene glycol, and water were then added while continuing to mix in the air tight tank/container sparged with nitrogen. Next, a calculated amount of THC- and CBD-containing particles were added to the excipient solution and mixed for about fifteen (15) minutes while continuing to be sparged with nitrogen in an airtight container. The balance of the dehydrated alcohol was added and mixed for about ten (10) minutes while the mixture continued to be sparged with nitrogen in an airtight container to give a final aqueous-based oral solution having 7.5% weight THC/CBD. The final aqueous-based oral solution was then filtered and filled into 30 ml amber glass bottles.

TABLE 3

Components of Oral Solution

| Component | Standard | Function | Wt % |
|---|---|---|---|
| BHA | USP | Antioxidant | 0.01 |
| Sucralose | NF | Sweetener | 0.05 |
| Methyl Paraben | USP | Preservative | 0.02 |
| Propyl Paraben | USP | Preservative | 0.02 |
| PEG 400 | USP | Co-solvent | 9.0 |
| Propylene Glycol | USP | Co-solvent | 3.5 |
| Water | USP | Solvent/Diluent | 29.9 |
| Cannabis mixture (THC:CBD 1:1) | | drug | 7.5 |
| Dehydrated Alcohol | USP | Co-solvent | 50 |

The invention claimed is:

1. An aqueous-based oral liquid formulation comprising a solvent comprising water, alcohol and propylene glycol and/or polyethylene glycol in an amount in the range of about 60-99% by wt, wherein the formulation comprises up to 40% by wt water, up to 65% by wt alcohol and up to 50% by wt propylene glycol and/or polyethylene glycol combined with pharmaceutical agent-containing particles of plant material in an amount in the range of about 1-40% by wt, wherein the pharmaceutical agent is selected from the group consisting of cannabinoids, cannabinoid derivatives, terpenes and mixtures thereof, and at least 50% by wt of the particles range in size from about 50 to about 2000 μm.

2. The formulation of claim 1, wherein the pharmaceutical agent is selected form the group consisting of cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), a naphthoylindole, a phenylacetylindole, a benzoylindole, a cyclohexylphenole, delta-9 tetrahydrocannabinol (THC or dronabinol), delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716) TWH-018, JWH-073, CP-55940, dimethylheptylpyran, HU-210, HU-331, SR144528, WIN 55,212-2, JWH-133, levonantradol, and AM-2201.

3. The formulation of claim 2, wherein the pharmaceutical agent is CBD, THC or a combination thereof.

4. The formulation of claim 1, wherein at least 75% by weight of the pharmaceutical particles have a size in the range of 300 to 750 μm.

5. The formulation of claim 1, wherein the plant material is *Cannabis* leaves.

6. The formulation of claim 1, wherein the pharmaceutical agent-containing particles comprise a water content of at least about 10%.

7. The formulation of claim 1, wherein the pharmaceutical agent-containing particles comprise a water content of 10-50%.

8. The formulation of claim 1, wherein the solvent comprises about 29.9% water by wt, about 50% alcohol by wt and a cosolvent comprising propylene glycol, polyethylene glycol or a combination thereof in an amount of from about 12.5% by wt.

9. The formulation of claim 1, comprising 7.5% by wt pharmaceutical agent-containing particles and solvent in an amount of greater than 90% by wt.

10. The formulation of claim 1, additionally comprising one or more of a sweetener, a colorant, a flavouring agent, or an anti-microbial agent.

* * * * *